United States Patent [19]
Metzger et al.

[11] 4,128,412
[45] Dec. 5, 1978

[54] HERBICIDAL COMPOSITION AND METHOD USING N-(2-ETHYLSULFONYL-1,3,4-THIADIAZOL-5-YL)-N-METHYL-N'-METHYL UREA

[75] Inventors: Carl Metzger, Wuppertal-Elberfeld; Ludwig Eue; Helmuth Hack, both of Cologne, All of Germany

[73] Assignee: Bayer Aktiengesellschaft, Leverkusen, Germany

[21] Appl. No.: 821,031

[22] Filed: Aug. 1, 1977

Related U.S. Application Data

[60] Division of Ser. No. 579,124, May 19, 1975, Pat. No. 4,049,670, which is a division of Ser. No. 247,176, Apr. 24, 1972, which is a continuation of Ser. No. 887,368, Dec. 22, 1969, abandoned.

[30] Foreign Application Priority Data

Dec. 23, 1968 [DE] Fed. Rep. of Germany ....... 1816568

[51] Int. Cl.$^2$ ........................ A01N 9/14; A01N 21/02
[52] U.S. Cl. ........................................................ 71/90
[58] Field of Search ..................... 71/90; 260/306.8 D

*Primary Examiner*—Alton D. Rollins
*Attorney, Agent, or Firm*—Sprung, Felfe, Horn, Lynch & Kramer

[57] ABSTRACT

1,3,4-Thiadiazol-5-yl-ureas, i.e. N-[2-(alkyl, alkylmercapto, alkenylmercapto alkynylmercapto, chloro-substituted benzylmercapto, carboxy-alkylmercapto, aminocarbonyl-alkylmercapto, chlorophenyl-aminocarbonyl-alkylmercapto, alkylsulfonyl, benzylsulfonyl and alkoxy)-1,3,4-thiadiazol-5-yl]-N-alkyl-[N'-mono- and N',N'-di-alkyl]-ureas, which possess herbicidal properties, and which may be produced by conventional methods.

2 Claims, No Drawings

HERBICIDAL COMPOSITION AND METHOD USING N-(2-ETHYLSULFONYL-1,3,4-THIADIAZOL-5-YL)-N-METHYL-N'-METHYL UREA

This is a divisional application of Ser. No. 579,124, filed May 19, 1975, now U.S. Pat. No. 4,049,670, which in turn is a divisional of application Ser. No. 247,176, filed Apr. 24, 1972, which in turn was a continuation of Ser. No. 887,368, filed Dec. 22, 1969, now abandoned.

The present invention relates to and has for its objects the provision for particular new 1,3,4-thiadiazol-5-yl-ureas, i.e. N-[2-(alkyl, alkylmercapto, alkenylmercapto, alkymylmercapto, chloro-substituted benzylmercapto, carboxyalkylmercapto, aminocarbonyl-alkylmercapto, chlorophenylaminocarbonyl-alkylmercapto, alkylsulfonyl, benzylsulfonyl and alkoxy)-1,3,4-thiadiazol-5-yl]-N-alkyl-[N'-mono- and N',N'-di- alkyl]ureas, which possess valuable, especially selective, herbicidal properties, active compositions in the form of mixtures of such compounds with solid and liquid dispersible carrier vehicles, and methods for producing such compounds and for using such compounds in a new way, especially for combating weeds, undesired plants, and the like, with other and further objects becoming apparent from a study of the within specification and accompanying examples.

It is known that thiazolyl-ureas, for example N-(4-methyl-1,3-thiazol-2-yl)-N'-methyl-urea (A), can be used as herbicides (see Belgian Pat. No. 679,138).

It has now been found, in accordance with the present invention, that the particular new 1,3,4-thiadiazol-5-yl-ureas of the formula:

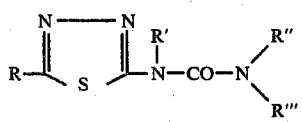  (I)

in which
R is alkyl of 1–4 carbon atoms, alkylmercapto of 1–4 carbon atoms, alkenylmercapto of 2–4 carbon atoms, alkynylmercapto of 2–4 carbon atoms, chloro-substituted benzylmercapto, carboxy-alkylmercapto having 1–4 carbon atoms in the alkylmercapto moiety, aminocarbonyl-alkylmercapto having 1–4 carbon atoms in the alkylmercapto moiety, chlorophenylaminocarbonyl-alkylmercapto having 1–4 carbon atoms in the alkylmercapto moiety, alkylsulfoxyl, alkylsulfonyl of 1–4 carbon atoms, benzylsulfonyl, or alkoxy of 1–4 carbon atoms, R' is alkyl of 1–4 carbon atoms, R" is hydrogen or alkyl of 1–4 carbon atoms, and R''' is alkyl of 1–4 carbon atoms, exhibit strong herbicidal, in particular selective herbicidal, properties.

It has been furthermore found, in accordance with the present invention, that a process for the production of the particular new compounds of formula (I) above may be provided, which comprises (a) reacting a 5-amino-1,3,4-thiadiazole of the formula:

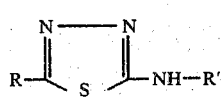  (II)

in which

R and R' are the same defined above, with an isocyanate of the formula

  (III)

in which

R''' is the same as defined above, or (b) reacting a compound of formula (II) above, in the presence of an acid-binding agent, with an acid chloride of the formula

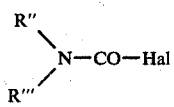  (IV)

in which

R" and R''' are the same as defined above, and

Hal is a halogen atom such as chloro, bromo, iodo and fluoro, especially chloro, or (c) reacting a urethane of the formula

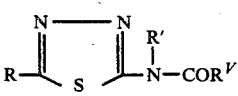  (V)

in which

R and R' are the same as defined above, and $R^V$ is methyl or phenyl, at elevated temperature, with an amine of the formula

  (VI)

in which

R" and R''' are the same as defined above.

It is decidedly surprising that the particular new compounds of formula (I) above according to the present invention exhibit a strong herbicidal activity and, in particular, a better selective herbicidal activity than the previously known compounds of analogous constitution and the same type of activity such as compound (A) noted above. The instant compounds according to the present invention therefore represent a valuable contribution to the art.

If 2-n-propyl-5-methylamino-1,3,4-thiadiazole and methyl-isocyanate are used as starting materials, the reaction course according to process variant (a) can be represented by the following formula scheme:

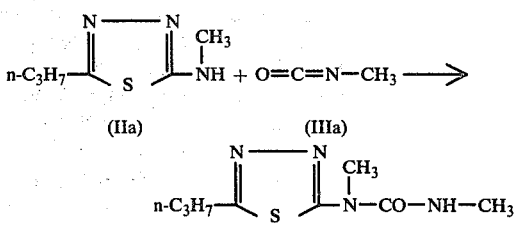

If dimethylcarbamic acid chloride is used for reaction with the same thiadiazole, the reaction course of process variant (b) can be represented by the following formula scheme:

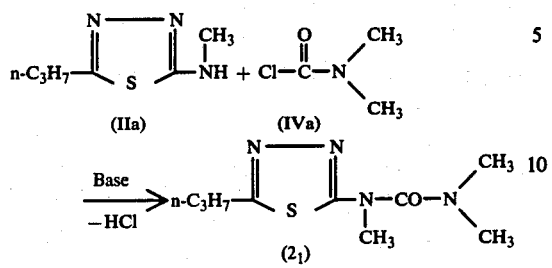

The reaction according to process variant (c) proceeds in an analogous manner:

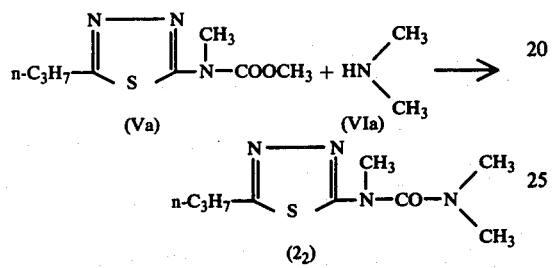

Advantageously, in accordance with the present invention, in the various formulae herein:

R represents straight and branched chain lower alkyl hydrocarbon of 1–4 carbon atoms such as methyl, ethyl, n- and isopropyl, n-, iso-, sec.- and tert.-butyl, and the like, especially $C_{1-3}$ or $C_{1-2}$ alkyl;

straight and branched chain lower alkylmercapto of 1–4 carbon atoms such as methyl to tert.-butyl inclusive, as defined above, and the like,-mercapto, especially $C_{1-3}$ or $C_{1-2}$ alkylmercapto;

straight and branched chain lower alkenylmercapto of 2–4 carbon atoms such as vinyl, α-, β and γ- allyl (i.e. prop-2-enyl, 1-methyl-vinyl and prop-1-enyl), but-1,2 and 3-enyl, 1-methyl-prop-1 and 2-enyl, and 2-methyl-prop-1 and 2-enyl, and the like, -mercapto, especially $C_{3-4}$ alkenylmercapto, more especially $C_3$ alkenylmercapto, and most especially γ-allylmercapto;

straight and branched chain lower alkynylmercapto of 2–4 carbon atoms such as acetylenyl, prop-1 and 2-ynyl, but 1,2 and 3-ynyl, 1-methyl-prop-2-ynyl, and the like, -mercapto, especially $C_{3-4}$ alkynylmercapto, more especially $C_3$ alkynylmercapto, and most especially prop-2-ynylmercapto;

chloro-substituted benzylmercapto such as 2-, 3- and 4-mono and 2,3-, 2,4-, 2,5-, 2,6-, 3,4- and 3,5- di chloro benzylmercapto, and the like, especially mono and di chloro substituted benzylmercapto, and more especially 4-mono and 3,4-di chloro benzylmercapto;

carboxy substituted-lower alkylmercapto having 1–4 carbon atoms in the alkylmercapto moiety such as ω-carboxymethyl, ethyl, n-propyl, n-butyl, and the like, -mercapto [i.e. $HOOC(CH_2)_{1-4}$—S—], especially ω-carboxy $C_{1-3}$ or $C_{1-2}$ (especially straight chain) alkylmercapto;

aminocarbonyl substituted-lower alkylmercapto having 1–4 carbon atoms in the alkylmercapto moiety such as ω-aminomethyl, ethyl, n-propyl, n-butyl, and the like, -mercapto [i.e. $NH_2CO(CH_2)_{1-4}$—S—], especially ω-aminocarbonyl $C_{1-3}$ or $C_{1-2}$ (especially straight chain) alkylmercapto;

chlorophenyl-aminocarbonyl substituted-lower alkylmercapto having 1–4 carbon atoms in the alkylmercapto moiety such as ω-(2-, 3- and 4- chloro-phenylaminocarbonyl)methyl, ethyl, n-propyl, n-butyl, and the like, -mercapto [i.e. $Cl—C_6H_4—NHCO(CH_2)_{1-4}$—S—], especially ω-(chlorophenylaminocarbonyl)-$C_{1-3}$ or $C_{1-2}$ (especially straight chain) alkylmercapto, and more especially ω-(4-chloro-phenyl-aminocarbonyl)$C_{1-3}$ or $C_{1-2}$ alkylmercapto;

straight and branched chain lower alkylsulfonyl of 1–4 carbon atoms such as methyl to tert.-butyl inclusive, as defined above, and the like, -sulfonyl, especially $C_{1-3}$ or $C_{1-2}$ alkylsulfonyl;

benzylsulfonyl; or straight and branched chain lower alkylsulfoxyl of 1–4 carbon atoms such as methyl to tert.-butyl inclusive, as defined above, and the like, -sulfoxyl, especially $C_{1-3}$ or $C_{1-2}$ alkylsulfoxyl;

benzylsulfoxyl; or straight and branched chain lower alkoxy of 1–4 carbon atoms such as methoxy, ethoxy, n- and isopropoxy, n-, iso-, sec.- and tert.-butoxy, and the like, especially $C_{1-3}$ or $C_{1-2}$ alkoxy;

R' represents straight and branched chain lower alkyl hydrocarbon of 1–4 carbon atoms such as methyl to tert.-butyl inclusive, as defined above, and the like, especially $C_{1-3}$ or $C_{1-2}$ alkyl;

R" represents hydrogen; or straight and branched chain lower alkyl hydrocarbon of 1–4 carbon atoms such as methyl to tert.-butyl inclusive, as defined above, and the like, especially $C_{1-3}$ or $C_{1-2}$ alkyl; and R''' represents straight and branched chain lower alkyl hydrocarbon of 1–4 carbon atoms such as methyl to tert.-butyl inclusive, as defined above, and the like, especially $C_{1-3}$ or $C_{1-2}$ alkyl.

Preferably, R is $C_{1-3}$ or $C_{1-2}$ alkyl; or $C_{1-4}$ or $C_{1-3}$ or $C_{1-2}$ alkylmercapto; or $C_{3-4}$ alkenylmercapto; or $C_{3-4}$ alkynylmercapto; or mono and di chloro-benzylmercapto; or ω-carboxy-$C_{1-3}$ or $C_{1-2}$ alkylmercapto; or ω-aminocarbonyl$C_{1-3}$ or $C_{1-2}$ alkylmercapto; or ω-chlorophenyl-aminocarbonyl$C_{1-3}$ or $C_{1-2}$ alkylmercapto; or $C_{1-4}$ or $C_{1-3}$ or $C_{1-2}$ alkylsulfonyl; or benzylsulfonyl; or $C_{1-3}$ or $C_{1-2}$ alkoxy; R' is $C_{1-4}$ or $C_{1-3}$ or $C_{1-2}$ alkyl; R" is hydrogen; or $C_{1-3}$ or $C_{1-2}$ alkyl; especially hydrogen; and R''' is $C_{1-3}$ or $C_{1-2}$ alkyl.

In particular, R is $C_{1-3}$ alkyl; or $C_{1-4}$ alkylmercapto; or allylmercapto; or propynylmercapto; or $C_{1-4}$ alkylsulfonyl; R' is $C_{1-3}$ alkyl; R" is hydrogen; and R''' is $C_{1-2}$ alkyl.

The thiadiazoles which may be used as starting materials are clearly defined by formula (II) above.

Examples of such alkylamino-thiadiazoles of formula (II) above which may be used as starting materials according to the present invention include: 2-propyl-5-methylamino-1,3,4-thiadiazole; 2-isopropyl-5-methylamino-1,3,4-thiadiazole; 2-ethylmercapto-5-ethylamino-1,3,4-thiadiazole; 2-propylmercapto-5-ethylamino-1,3,4-thiadiazole; 2-ethylmercapto-5-methylamino-1,3,4-thiadiazole; 2-n-butylmercapto-5-methylamino-1,3,4-thiadiazole; 2-allylmercapto-5-methylamino-1,3,4-thiadiazole; and the like.

Some of the thiadiazole compounds of formula (II) above are already known. The still new starting thiadiazoles can be prepared in the same manner as the already known ones, for example by reaction of the appropriate 1-acyl-thiosemicarbazides with agents which split off water, such as acetic anhydride (see Chemische Berichte 29, 2511 (1896)).

The isocyanates which may be used as starting materials are clearly defined by formula (III) above.

Examples of such isocyanates of formula (III) above which may be used as starting materials according to the present invention include: methylisocyanate, ethylisocyanate, isopropylisocyanate, and the like.

The acid chlorides which may be used as starting materials are clearly defined by formula (IV) above.

Examples of such acid chlorides of formula (IV) above which may be used as starting materials according to the present invention include: dimethylcarbamic acid chloride, and the like.

The urethanes which may be used as starting materials are clearly defined by formula (V) above.

Furthermore, the amines which may be used as starting materials are clearly defined by formula (VI) above.

The starting materials of formulae (III), (IV), (V) and (VI) are already known.

In the following, further details for the carrying out of the three process variants are given:

Each of the production process variants of the present invention is preferably carried out in the presence of a solvent (which term includes mere diluents). In this regard, all inert organic solvents are suitable. The preferred solvents include hydrocarbons, such as benzene, toluene; ethers, such as diethyl ether, dioxan, tetrahydrofuran chlorinate hydrocarbons, such as methylene chloride, chloroform, carbon tetrachloride; ketones, such as acetone; esters, such as ethyl acetate, and acetonitrile and dimethyl formamide; and the like.

As the acid-binding agent for reaction variant (b), any customary acid-binder can be used. The preferred acid-binding agents include alkali metal hydroxides, alkali metal carbonates and tertiary amines. Particularly suitable are sodium hydroxide, sodium carbonate, triethylamine, pyridine, and the like.

The reaction temperatures for each of the process variants can be varied within a fairly wide range. In general, the reaction is carried out at substantially between about 0°–140° C., and preferably between about 10°–120° C.

When carrying out the production process variants according to the present invention, approximately equimolar amounts of the starting materials are generally used. The working up of the reaction mixture is effected in the customary manner.

Advantageously, the active compounds according to the present invention exhibit strong herbicidal properties and can therefore be used for the control of weeds. By weeds are meant in the widest sense all plants which grow in places where they are not desired. Whether the active compounds according to the present invention act as total or selective herbicides depends essentially on the amount applied, as the artisan will appreciate.

The active compounds according to the present invention can be used for example in the case of the following plants: dicotyledons, such as mustard (Sinapis), cress (Lepidium), cleaver (Galium), common chickweed (Stellaria), mayweed (Matricaria), smallflower Galinsoga (Galinsoga), fathen (Chenopodium), stinging nettle (Urtica), groundsel (Senecio), cotton (Gossypium), beets (Beta), carrots (Daucus), beans (Phaseolus), potatoes (Solanum), coffee (Coffea); monocotyledons, such as timothy (Phleum), bluegrass (Poa), fescue (Festuca), goosegrass (Eleusine), foxtail (Setaria), ryegrass (Lolium), cheat (Bromus), barnyard grass (Echinochloa), maize (Zea), rice (Oryza), oats (Avena), barley (Hordeum), wheat (Triticum), millet (Panicum) and sugar cane (Saccharum); and the like.

The instant active compounds are particularly well suited for selective weed control in cereals, cotton and carrots.

Appropriately, the instant active compounds also have only a comparatively slight toxicity to warm-blooded animals.

The instant active compounds also exhibit bactericidal effectiveness and can therefore be used for example in industrial disinfection endeavors.

The active compounds according to the instant invention can be utilized, if desired, in the form of the usual formulations or compositions with conventional inert (i.e. plant compatible or herbicidally inert) pesticide diluents or extenders, i.e. diluents or extenders of the type usable in conventional pesticide formulations or compositions, e.g. conventional pesticide dispersible carrier vehicles, such as solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: inert dispersible liquid diluent carriers including inert organic solvents, such as aromatic hydrocarbons (e.g. benzene, toluene, xylene, etc.), halogenated, especially chlorinated, aromatic hydrocarbons (e.g. chloro-benzenes), paraffins (e.g. petroleum fractions), chlorinated aliphatic hydrocarbons (e.g. methylene chloride, etc.), alcohols (e.g. methanol, ethanol, propanol, butanol, etc.), ethers, ether-alcohols (e.g. glycol monomethyl ether, etc.), amines (e.g. ethanol-amine, etc.), amides (e.g. dimethyl formamide, etc.), sulfoxides (e.g. dimethyl sulfoxide, etc.), ketones (e.g. acetone, etc.), and/or water; as well as inert dispersible finely divided solid carriers, such as ground natural minerals (e.g. kaolins, alumina, silica, chalk, i.e. calcium carbonate, talc, kieselguhr, etc.), and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfonates, aryl sulfonates, etc., and especially alkyl aryl-polyglycol ethers, magnesium stearate, sodium oleate, etc.); and/or dispersing agents, such as lignin, sulfite waste liquors, methyl cellulose, etc.

As will be appreciated by the artisan, the active compounds according to the instant invention may be employed alone or in the form of mixtures with one another and/or with such solid and/or liquid dispersible carrier vehicles and/or with other known compatible active agents, especially plant protection agents, such as other herbicides, or fungicides, insecticides, bactericides, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1 and 95% by weight, and preferably 0.5 and 90% by weight, of the mixture, whereas carrier composition mixtures suitable for direct application or field application generally contemplate those in which the active compound is present in an amount substantially between about 0.005–0.5%, preferably 0.008–0.1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.005–95%, and preferably 0.008–95%, by weight of the mixture.

Suitably, the amount of active compound applied per unit area varies according to the purpose intended, i.e. the effect desired, and the mode of application. In general, substantially between about 1–50 kg of active compound per hectare are applied, and preferably between about 2–20 kg of active compound per hectare, irrespective of the presence or absence of the carrier vehicle, i.e. whether for post-emergence application to the weeds or undesired plants or for pre-emergence application to the soil.

The active compounds can also be used in accordance with the well-known ultra-low-volume process with good success, i.e. by applying such compound if normally a liquid, or by applying a liquid composition containing the same, via very effective atomizing equipment in finely divided form, e.g. average particle diameter of from 50–100 microns, or even less, i.e. mist form, for example by airplane crop spraying techniques. Only up to at most about a few liters/hectare are needed, and often amount only up about 1 quart/acre, preferably 2–16 fluid ounces/acre, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

While the active compounds can be used effectively according to the pre-emergence method, they are also particularly effective when used according to the post-emergence method.

Furthermore, the present invention contemplates methods of selectively killing, combatting or controlling undesired plants, e.g. weeds and the like, which comprise applying to at least one of (a) such weeds and (b) their habitat, i.e. the locus to be protected, a herbicidally effective or toxic amount of the particular active compound of the invention alone or together with a carrier vehicle as noted above. The instant formulations or compositions are applied in the usual manner, for example by spraying, atomizing, scattering, dusting, watering, sprinkling, and the like, whether for pre-emergence application to the soil or post-emergence application to the weeds.

It will be realized, of course, that in connection with the pre-emergence use of the instant compounds as well as the post-emergence use thereof, the concentration of the particular active compound utilized in admixture with the carrier vehicle will depend upon the intended application and may be varied within a fairly wide range depending upon the weather conditions, the purpose for which the active compound is used, e.g. for total or only selective herbicidal effect, and the plants which are to be controlled or protected. Therefore, in special cases, it is possible to go above or below the aforementioned concentration ranges and ranges of amounts per unit area.

The following Examples illustrate, without limitation, the herbicidal activity of the particular active compounds of the present invention.

EXAMPLE 1

Pre-emergence test

Solvent: 5 parts by weight acetone
Emulsifier: 1 part by weight alkylaryl polyglycol ether To produce a suitable preparation of the particular active compound, 1 part by weight of such active compound is mixed with the stated amount of solvent, the stated amount of emulsifier is added thereto, and the resulting concentrate is then diluted with water to the desired final concentration.

Seeds of the test plants are sown in normal soil and, after 24 hours, watered with the preparation of the given active compound. It is expedient to keep constant the amount of water per unit area. The concentration of the given active compound in the given preparation is of no importance, only the amount of active compound applied per unit area being decisive. After three weeks, the degree of damage to the test plants is determined and characterized by the values 0–5, which have the following meaning:

0: no effect
1: slight damage or delay in growth
2: marked damage or inhibition of growth
3: heavy damage and only deficient development or only 50% emerged
4: plants partially destroyed after germination or only 25% emerged
5: plants completely dead or not emerged.

The particular active compounds tested, the amounts applied and the results obtained can be seen from the following Table 1:

Table 1

| Active compound | Amount of active compound applied in kg/hectare | Pre-emergence test | | | | | | | | | | |
|---|---|---|---|---|---|---|---|---|---|---|---|---|
| | | Sinapis | Echinochloa | Chenopodium | Stellaria | Galinsoga | Matricaria | Oats | Cotton | Wheat | Maize |
| (A) CH₃—[structure]—NH—CO—NH—CH₃ (known) | 10 / 5 / 2.5 | 4 / 3 / 1 | 4 / 3 / 2 | 5 / 4 / 2-3 | — / — | — / — | — / — | 3-4 / 3 / 2 | 3 / 1 / 0 | 4 / 3 / 1 | — / — |
| (3₁) C₂H₅—[structure] N(C₂H₅)—CO—NH—CH₃ | 10 / 5 / 2.5 | 5 / 5 / 5 | 5 / 5 / 5 | 5 / 5 / 5 | 5 / 5 / 5 | 5 / 5 / 5 | 5 / 5 / 5 | 5 / 5 / 4 | 5 / 5 / 4 | 5 / 4-5 / 4 | 3 / 5 / 4 |
| (4₁) n-C₃H₇—[structure] N(C₂H₅)—CO—NH—CH₃ | 10 / 5 / 2.5 | 5 / 5 / 4 | 5 / 5 / 4 | 5 / 5 / 5 | 5 / 5 / 4-5 | 5 / 5 / 5 | 5 / 5 / 5 | 3 / 2 / 1 | 2 / 1 / 0 | 2 / 1 / 0 | 4 / 3 / 2 |
| (5₁) i-C₃H₇—[structure] N(C₂H₅)—CO—NH—CH₃ | 10 / 5 / 2.5 | 4 / 4 / 3 | 5 / 4-5 / 4 | 5 / 5 / 4 | 5 / 5 / 4 | 5 / 5 / 5 | 5 / 5 / 4-5 | 4 / 4 / 3 | 5 / 4 / 4 | 3 / 1 / 0 | 3-4 / 3 / 2 |
| (6₁) CH₂=CH—CH₂—[structure] N(C₂H₅)—CO—NH—CH₃ | 10 / 5 / 2.5 | 4 / 4 / 3 | 5 / 5 / 4 | 5 / 5 / 5 | 5 / 5 / 3 | 5 / 5 / 5 | 5 / 5 / 5 | 4 / 3 / 2 | 4 / 3 / 2 | 3 / 1 / 0 | 2 / 0 / 0 |
| (7₁) n-C₃H₇—[structure] N(CH₃)—CO—NH—CH₃ | 10 / 5 / 2.5 | 5 / 5 / 4 | 4-5 / 4 / 3 | 5 / 5 / 5 | 5 / 5 / 4 | 5 / 5 / 5 | 5 / 5 / 5 | 5 / 5 / 4 | 5 / 4-5 / 4 | 5 / 4 / 3 | 5 / 4 / 3 |
| (8₁) n-C₄H₉—[structure] N(CH₃)—CO—NH—CH₃ | 10 / 5 / 2.5 | 4-5 / 4 / 3 | 4-5 / 4-5 / 3 | 5 / 5 / 5 | 5 / 5 / 4 | 5 / 5 / 5 | 5 / 5 / 4 | 4 / 3 / 2 | 3 / 3 / 2 | 3 / 2 / 1 | 2 / 1 / 0 |
| (9₁) CH≡C—CH₂—[structure] N(CH₃)—CO—NH—CH₃ | 10 / 5 / 2.5 | 5 / 4-5 / 4 | 5 / 5 / 5 | 5 / 5 / 5 | 5 / 5 / 5 | 5 / 5 / 4 | 5 / 5 / 5 | 4-5 / 3 / 4 | 3 / 2 / 0 | 3 / 1 / 0 | 3 / 1 / 0 |
| (1₁) n-C₃H₇—[structure] N(CH₃)—CO—NH—CH₃ | 10 / 5 / 2.5 | 5 / 5 / 3 | 5 / 5 / 5 | 5 / 5 / 5 | 5 / 5 / 4 | 5 / 5 / 4 | 5 / 5 / 5 | 4 / 3 / 2 | 3 / 2 / 2 | 2 / 1 / 0 | 2 / 0 / 0 |
| (10₁) i-C₃H₇—[structure] N(CH₃)—CO—NH—CH₃ | 10 / 5 / 2.5 | 5 / 5 / 5 | 5 / 5 / 4 | 5 / 5 / 5 | 5 / 5 / 5 | 5 / 5 / 5 | 5 / 5 / 4 | 5 / 4-5 / 4-5 | 4 / 3 / 3 | 5 / 4 / 4 | 5 / 4 / 3 |
| (11₁) i-C₃H₇—[structure] N(C₂H₅)—CO—NH—CH₃ | 10 / 5 / 2.5 | 4 / 3 / 3 | 5 / 5 / 4 | 5 / 5 / 5 | 5 / 5 / 5 | 5 / 5 / 4 | 5 / 5 / 4 | 5 / 4 / 4 | 2 / 1 / 0 | 4 / 3 / 3 | 3 / 1-2 / 0 |

Table 1-continued

Pre-emergence test

| Active compound | Amount of active compound applied in kg/hectare | Sinapis | Echinochloa | Chenopodium | Stellaria | Galinsoga | Matricaria | Oats | Cotton | Wheat | Maize |
|---|---|---|---|---|---|---|---|---|---|---|---|
| (12₁) CH₃SO₂—[ring]—N(CH₃)—N—CO—N(H)(CH₃) | 10 / 5 / 2.5 | 5 / 5 / 4 | 5 / 5 / 5 | 5 / 5 / 5 | 5 / 5 / 5 | 5 / 5 / 5 | 5 / 5 / 5 | 3 / 2 / 0 | 3 / 1-2 / 0 | 4 / 3 / 2 | 3 / 2 / 1 |
| (13₁) CH₃SO₂—[ring]—N(C₂H₅)—N—CO—N(H)(CH₃) | 10 / 5 / 2.5 | 5 / 5 / 5 | 5 / 5 / 5 | 5 / 5 / 5 | 5 / 5 / 5 | 5 / 5 / 5 | 5 / 5 / 5 | 5 / 5 / 4 | 5 / 5 / 4 | 5 / 4-5 / 4-5 | 5 / 5 / 4-5 |
| (14₁) C₂H₅SO₂—[ring]—N(CH₃)—N—CO—N(H)(CH₃) | 10 / 5 / 2.5 | 5 / 5 / 5 | 5 / 5 / 5 | 5 / 5 / 5 | 5 / 5 / 5 | 5 / 3 / 3 | 5 / 5 / 5 | 3 / 5 / 5 | 5 / 5 / 5 | 5 / 3 / 3 | 5 / 5 / 5 |
| (15₁) n-C₃H₇SO₂—[ring]—N(CH₃)—N—CO—N(H)(CH₃) | 10 / 5 / 2.5 | 5 / 5 / 4 | 5 / 5 / 5 | 5 / 5 / 5 | 5 / 5 / 5 | 5 / 3 / 3 | 5 / 5 / 5 | 3 / 2 / 1 | 3 / 2 / 1 | 2 / 1 / 0 | 5 / 4 / 2-3 |
| (16₁) i-C₃H₇SO₂—[ring]—N(CH₃)—N—CO—N(H)(CH₃) | 10 / 5 / 2.5 | 5 / 5 / 5 | 5 / 5 / 4-5 | 5 / 5 / 4 | 5 / 5 / 5 | 5 / 5 / 5 | 5 / 5 / 4-5 | 5 / 4-5 / 4-5 | 5 / 4 / 3 | 4-5 / 4 / 4 | 5 / 4 / 4 |

EXAMPLE 2

Post-emergence test

Solvent: 5 parts by weight acetone
Emulsifier: 1 part by weight alkylaryl polyglycol ether To produce a suitable preparation of the particular active compound, 1 part by weight of such active compound is mixed with the stated amount of solvent, the stated amount of emulsifier is added thereto, and the resulting concentrate is then diluted with water to the desired final concentration.

Test plants which have a height of about 5-15 cm. are sprayed with the preparation of the given active compound in such a way that the amounts of active compound per unit area as given in the following table are used. Depending on the concentration of the spraying liquor the amount of water ranges from 1000-2000 l/ha. After 3 weeks, the degree of damage to the plants is determined and characterized by the values 0-5, which have the following meaning:

0: no effect
1: a few slightly burnt spots
2: marked damage to leaves
3: some leaves and parts of stalks partially dead
4: plant partially destroyed
5: plant completely dead The particular active compounds tested, their concentrations, and the results obtained can be seen from the following Table 2:

Table 2

Post-emergence test

| Active compound | Amount of active compound applied in kg/hectare | Echinochloa | Chenopodium | Sinapis | Galinsoga | Stellaria | Urtica | Matricaria | Oats | Cotton | Wheat | Carrots |
|---|---|---|---|---|---|---|---|---|---|---|---|---|
| (A) CH₃—⟨N=⟩—S—NH—CO—NH—CH₃ (known) | 4 | 4 | 5 | 5 | 5 | 4-5 | 3 | — | 1-2 | 2-3 | 1-2 | 3 |
|  | 2 | 3 | 4-5 | 4-5 | 4-5 | 3 | 1 | — | 1 | 2 | 1 | 1 |
|  | 1 | 1 | 3 | 4 | 3 | 2 | 0 | — | 0 | 0 | 0 | 0 |
| (3₂) C₂H₅—S—⟨N=⟩—N(C₂H₅)—CO—NH—CH₃ | 4 | 5 | 5 | 5 | 5 | 5 | 5 | 5 | 5 | 5 | 5 | 5 |
|  | 2 | 5 | 5 | 5 | 5 | 5 | 5 | 5 | 5 | 5 | 4-5 | 5 |
|  | 1 | 5 | 5 | 5 | 5 | 5 | 5 | 5 | 4-5 | 5 | 4 | 5 |
| (4₂) n-C₃H₇—S—⟨N=⟩—N(C₂H₅)—CO—NH—CH₃ | 4 | 5 | 5 | 5 | 5 | 5 | 5 | 5 | 5 | 5 | 5 | 5 |
|  | 2 | 5 | 5 | 5 | 5 | 5 | 5 | 5 | 5 | 5 | 4-5 | 5 |
|  | 1 | 4-3 | 4-5 | 4 | 3 | 5 | 5 | 4 | 4 | 5 | 3-4 | 3 |
| (5₂) i-C₃H₇—S—⟨N=⟩—N(C₂H₅)—CO—NH—CH₃ | 2 | 5 | 5 | 5 | 5 | 5 | 5 | 5 | 5 | 5 | 4 | 5 |
|  | 1 | 4 | 5 | 5 | 5 | 5 | 5 | 5 | 5 | 5 | 3 | 5 |
|  | 0.5 | 3-4 | 4 | 5 | 4 | 5 | 5 | 4 | 4 | 5 | 3 | 3 |
| (17₁) —S—⟨N=⟩—N(CH₃)—CO—NH—CH₃ | 2 | 5 | 5 | 5 | 5 | 5 | 5 | 5 | 5 | 5 | 4-5 | 5 |
|  | 1 | 5 | 5 | 5 | 5 | 5 | 5 | 5 | 5 | 5 | 3 | 5 |
|  | 0.5 | 5 | 5 | 5 | 5 | 5 | 5 | 5 | 5 | 5 | 3 | 3 |
| (8₂) n-C₄H₉—S—⟨N=⟩—N(CH₃)—CO—NH—CH₃ | 2 | 5 | 5 | 5 | 5 | 5 | 5 | 5 | 5 | 5 | 2 | 5 |
|  | 1 | 5 | 5 | 5 | 5 | 5 | 5 | 5 | 4 | 5 | 0 | 5 |
|  | 0.5 | 5 | 5 | 5 | 5 | 5 | 5 | 4 | 1 | 5 | 0 | 5 |
| (18₁) CH₂=CH—CH₂—S—⟨N=⟩—N(CH₃)—CO—NH—CH₃ | 2 | 5 | 5 | 5 | 5 | 5 | 5 | 5 | 5 | 5 | 4 | 5 |
|  | 1 | 5 | 5 | 5 | 5 | 5 | 5 | 5 | 4 | 5 | 4 | 5 |
|  | 0.5 | 4-5 | 5 | 5 | 4 | 5 | 5 | 4 | 4 | 4 | 2 | 5 |
| (19₁) CH₃S—S—⟨N=⟩—N(CH₃)—CO—NH—CH₃ | 2 | 5 | 5 | 5 | 5 | 5 | 5 | 5 | 5 | 4-5 | 5 | 5 |
|  | 1 | 5 | 5 | 5 | 5 | 5 | 5 | 4-5 | 4-5 | 4-5 | 5 | 4-5 |
|  | 0.5 | 5 | 5 | 5 | 5 | 5 | 5 | 3 | 3 | 4-5 | 3 | 4-5 |
| (10₂) i-C₃H₇—S—⟨N=⟩—N(CH₃)—CO—NH—CH₃ | 2 | 5 | 5 | 5 | 5 | 5 | 5 | 5 | 5 | 5 | 5 | 5 |
|  | 1 | 5 | 5 | 5 | 5 | 5 | 5 | 5 | 5 | 5 | 4 | 5 |
|  | 0.5 | 5 | 5 | 5 | 5 | 5 | 5 | 5 | 4 | 4 | 2 | 5 |
| (12₂) CH₃SO₂—S—⟨N=⟩—N(C₂H₅)—CO—N(H)(CH₃) | 4 | 5 | 5 | 5 | 5 | 5 | 5 | 5 | 5 | 5 | 5 | 5 |
|  | 2 | 5 | 5 | 5 | 5 | 5 | 5 | 5 | 5 | 5 | 4-5 | 5 |
|  | 1 | 5 | 5 | 5 | 5 | 5 | 5 | 5 | 4 | 5 | 4 | 3 |
| (13₂) CH₃SO₂—S—⟨N=⟩—N(C₂H₅)—CO—N(H)(CH₃) | 4 | 5 | 5 | 5 | 5 | 5 | 5 | 5 | 5 | 5 | 4 | 5 |
|  | 2 | 5 | 5 | 5 | 5 | 5 | 5 | 5 | 4-5 | 5 | 4 | 5 |
|  | 1 | 5 | 5 | 5 | 5 | 5 | 5 | 5 | 4 | 5 | 3 | 5 |

Table 2-continued

| Active compound | Amount of active compound applied in kg/hectare | Post-emergence test | | | | | | | | | | | |
|---|---|---|---|---|---|---|---|---|---|---|---|---|---|
| | | Echinochloa | Chenopodium | Sinapis | Galinsoga | Stellaria | Urtica | Matricaria | Oats | Cotton | Wheat | Carrots |
| (14₂) C₂H₅SO₂—[structure] | 4<br>2<br>1 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>4-5<br>4 | 5<br>5<br>5 | 4-5<br>4<br>3 | 5<br>5<br>5 |
| (15₂) n-C₃H₇SO₂—[structure] | 4<br>2<br>1 | 5<br>5<br>5 | 5<br>5<br>5 | 5<br>5<br>5 | 5<br>5<br>5 | 5<br>5<br>5 | 5<br>5<br>5 | 5<br>5<br>5 | 4-5<br>4-5<br>3 | 5<br>5<br>5 | 4-5<br>4<br>3 | 5<br>5<br>5 |
| (16₂) i-C₃H₇SO₂—[structure] | 4<br>2<br>1 | 5<br>5<br>5 | 5<br>5<br>5 | 5<br>5<br>5 | 5<br>5<br>5 | 5<br>5<br>5 | 5<br>5<br>5 | 5<br>5<br>5 | 5<br>5<br>4 | 5<br>5<br>5 | 4-5<br>4<br>4 | 5<br>5<br>5 |
| (20₁) n-C₄H₉SO₂—[structure] | 4<br>2<br>1 | 5<br>5<br>5 | 5<br>5<br>5 | 5<br>5<br>5 | 5<br>5<br>5 | 5<br>5<br>5 | 5<br>5<br>5 | 5<br>5<br>5 | 4-5<br>3<br>1 | 5<br>5<br>5 | 2-3<br>1<br>0 | 5<br>5<br>5 |

The following further examples are set forth to illustrate, without limitation, the manner of producing the instant active compounds according to the present invention.

EXAMPLE 3 [reaction variant (a)]

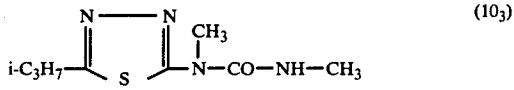

(10₃)

7.2 g (0.126 mol) methylisocyanate are added dropwise to 19.7 g (0.126 mol) 2-isopropyl-5-methylamino-1,3,4-thiadiazole in 100 ml ethyl acetate. After subsidence of the heat effect, heating under reflux is continued for a further 4 hours. After the solvent has been distilled off, the crude N-(2-isopropyl-1,3,4-thiadiazol-5-yl)-N,N'-dimethyl-urea is recrystallized from petroleum ether/acetone. m.p. 112° C.

In analogous manner, the following further ureas of formula (I) above according to the present invention are also prepared:

Table 3

| Compound No. | R | R' | R" | R''' | m.p. |
|---|---|---|---|---|---|
| (1₃) | n-C₃H₇ | CH₃ | H | CH₃ | 105° C |
| (21₁) | n-C₃H₇ | C₂H₅ | H | CH₃ | 98° C |
| (11₂) | i-C₃H₇ | C₂H₅ | H | CH₃ | 70° C |
| (19₂) | CH₃S | CH₃ | H | CH₃ | 163° C |
| (22₁) | CH₃S | C₂H₅ | H | CH₃ | 134° C |
| (17₂) | C₂H₅S | CH₃ | H | CH₃ | 84° C |
| (3₃) | C₂H₅S | C₂H₅ | H | CH₃ | 77° C |
| (7₂) | n-C₃H₇S | CH₃ | H | CH₃ | 85° C |
| (4₃) | n-C₃H₇S | C₂H₅ | H | CH₃ | 90° C |
| (23₁) | i-C₃H₇S | CH₃ | H | CH₃ | 102° C |
| (5₃) | i-C₃H₇S | C₂H₅ | H | CH₃ | 81° C |
| (8₃) | n-C₄H₉S | CH₃ | H | CH₃ | 82° C |
| (24₁) | n-C₄H₉S | C₂H₅ | H | CH₃ | 77° C |
| (18₂) | CH₂=CHCH₂S | CH₃ | H | CH₃ | 60° C |
| (6₂) | CH₂=CHCH₂S | C₂H₅ | H | CH₃ | 88° C |
| (9₂) | CH≡CCH₂S | CH₃ | H | CH₃ | 136° C |
| (25₁) | CH≡CCH₂S | C₂H₅ | H | CH₃ | 104° C |
| (26₁) | CH₃S | n-C₃H₇ | H | CH₃ | 113° C |
| (27₁) | CH₃S | iso-C₃H₇ | H | CH₃ | 114° C |
| (28₁) | CH₃S | n-C₄H₉ | H | CH₃ | 122° C |
| (19₁) | CH₃S | iso-C₄H₉ | H | CH₃ | 128° C |
| (12₂) | CH₃SO₂ | CH₃ | H | CH₃ | 184° C |
| (13₃) | CH₃SO₂ | C₂H₅ | H | CH₃ | 139° C |
| (14₃) | C₂H₅SO₂ | CH₃ | H | CH₃ | 157° C |
| (30₁) | C₂H₅SO₂ | C₂H₅ | H | CH₃ | 172° C |
| (15₃) | n-C₃H₇SO₂ | CH₃ | H | CH₃ | 146° C |
| (16₃) | i-C₃H₇SO₂ | CH₃ | H | CH₃ | 178° C |
| (31₁) | i-C₃H₇SO₂ | C₂H₅ | H | CH₃ | 141° C |
| (32₁) | n-C₃H₇SO₂ | C₂H₅ | H | CH₃ | 132° C |
| (20₂) | n-C₄H₉SO₂ | CH₃ | H | CH₃ | 129° C |
| (33₁) | n-C₄H₉SO₂ | C₂H₅ | H | CH₃ | 163° C |
| (34₁) | C₂H₅S | n-C₃H₇ | H | CH₃ | oily |
| (35₁) | C₂H₅S | i-C₃H₇ | H | CH₃ | oily |
| (36₁) | C₂H₅S | i-C₄H₉ | H | CH₃ | 73° C |
| (37₁) | CH₃O | CH₃ | H | CH₃ | 160° C |
| (38₁) | CH₃O | C₂H₅ | H | CH₃ | 140° C |
| (39₁) | n-C₃H₇O | C₂H₅ | N | CH₃ | 132° C |
| (40₁) | i-C₃H₇O | C₂H₅ | H | CH₃ | 134° C |
| (41₁) | p-Cl—C₆H₄—CH₂S | CH₃ | H | CH₃ | 135° C |
| (42₁) | p-Cl—C₆H₄—CH₂S | C₂H₅ | H | CH₃ | 136° C |
| (43₁) | 3,4-Cl₂—C₆H₃CH₂S | CH₃ | H | CH₃ | 94° C |
| (44₁) | C₆H₅—CH₂SO₂ | CH₃ | H | CH₃ | 195° C |
| (45₁) | HOOC—CH₂CH₂S | C₂H₅ | H | CH₃ | 122° C |
| (46₁) | H₂NCO—CH₂CH₂S | CH₃ | H | CH₃ | 174° C |
| (47₁) | N₂WCO—CH₂CH₂S | C₂H₅ | H | CH₃ | 100° C |
| (48₁) | p-Cl—C₆H₄—NWCO—CH₂CH₂S | CH₃ | H | CH₃ | 224° C |
| (49₁) | p-Cl—C₆H₄—HMCO—CN₂CH₂S | C₂H₅ | H | CH₃ | 176° C |
| (2₃) | n-C₃H₇ | CH₃ | CH₃ | CH₃ | 98° C |
| (50₁) | C₂H₅SO | C₂H₅ | H | CH₃ | 172° C |

Typical preferred compounds of the present invention includes:

(1) N-(2-n-propyl-1,3,4-thiadiazol-5-yl)-N,N'-dimethyl-urea (3) N-(2-ethylmercapto-1,3,4-thiadiazol-5-yl)-N-ethyl-N'-methyl urea (4) N-(2-n-propylmercapto-1,3,4-thiadiazol-5-yl)-N-ethyl-N'-methyl-urea (5) N-(2-isopropylmercapto-1,3,4-thiadiazol-5-yl)-N-ethyl-N'-methyl-urea (6) N-(2-prop-2'-enylmercapto-1,3,4-thiadiazol-5-yl)-N-ethyl-N'-methyl-urea (9) N-(2-prop-2'-ynylmercapto-1,3,4-thiadiazol-5-yl)-N,N'-dimethyl-urea

(12) N-(2-methylsulfonyl-1,3,4-thiadiazol-5-yl)-N,N'-dimethyl-urea

It will be realized by the artisan that all of the foregoing compounds contemplated by the present invention possess the desired selective or total herbicidal properties, and especially the capability of selectively destroying weeds, as well as a comparatively low toxicity toward warm-blooded creatures and a concomitantly low phytotoxicity with respect to higher plants, enabling such compounds to be used with correspondingly favorable compatibility with respect to warm-blooded creatures and higher plants for more effective control and/or elimination of weeds by selective application of such compounds to such weeds and/or their habitat. Nevertheless, the instant compounds possess total herbicidal action when used in large quantities, although selective herbicidal action is obtained when used in smaller quantities. As contemplated herein, the term "weeds" is meant to include not only weeds in the narrow sense, but also in the broad sense, whereby to cover all plants and vegetation considered undesirable for the particular purposes in question.

It will be appreciated that the instant specification and examples are set forth by way of illustration and not limitation, and that various modifications and changes may be made without departing from the spirit and scope of the present invention which is to be limited only by the scope of the appended claims.

What is claimed is:

1. Method of combating undesired vegetation which method comprises applying to common weeds and crops and their habitat herbicidally effective amounts of N-(2-ethylsulfonyl-1,3,4-thiadiazol-5-yl)-N-methyl-N'-methyl urea.

2. A composition for combatting undesired vegetation which comprises an herbicidally acceptable carrier and in amount effective to kill common weeds and/or crops, N-(2-ethylsulfonyl-1,3,4-thiadiazol-5-yl)-N-methyl-N'-methyl urea.

* * * * *